United States Patent
Paterson et al.

(10) Patent No.: US 8,444,596 B2
(45) Date of Patent: May 21, 2013

(54) BREAST MILK COLLECTION APPARATUS AND COMPONENTS THEREOF

(75) Inventors: Graeme L. J. Paterson, Cheddar (GB); Ralph J. Farrer, Bristol (GB); Koji Matsutori, Arlington, VA (US)

(73) Assignee: Lansinoh Laboratories, Inc., Alexandria, VA (US)

( * ) Notice: Subject to any disclaimer, the term of this patent is extended or adjusted under 35 U.S.C. 154(b) by 169 days.

(21) Appl. No.: 12/802,802

(22) Filed: Jun. 15, 2010

(65) Prior Publication Data

US 2010/0324477 A1    Dec. 23, 2010

Related U.S. Application Data

(60) Provisional application No. 61/269,283, filed on Jun. 22, 2009.

(51) Int. Cl.
*A61M 1/06*    (2006.01)

(52) U.S. Cl.
USPC .......................................................... 604/74

(58) Field of Classification Search
USPC .......................................................... 604/74
See application file for complete search history.

(56) References Cited

U.S. PATENT DOCUMENTS

| | | | |
|---|---|---|---|
| 4,799,922 A | 1/1989 | Beer et al. ........................ 604/74 |
| 4,809,589 A * | 3/1989 | Bertrand ........................ 92/98 R |
| 6,189,755 B1 * | 2/2001 | Wakefield ...................... 224/542 |
| 6,723,066 B2 | 4/2004 | Larsson et al. ................... 604/74 |
| 7,363,850 B2 | 4/2008 | Becker .......................... 92/103 F |
| 7,413,557 B2 | 8/2008 | Samson et al. ................... 604/74 |
| 2001/0038799 A1 * | 11/2001 | Silver et al. ..................... 417/515 |
| 2002/0198489 A1 * | 12/2002 | Silver et al. ...................... 604/74 |
| 2004/0087898 A1 * | 5/2004 | Weniger ........................... 604/74 |
| 2006/0111664 A1 * | 5/2006 | Samson et al. ................... 604/74 |
| 2007/0078383 A1 * | 4/2007 | Tashiro et al. .................... 604/74 |

FOREIGN PATENT DOCUMENTS

| WO | WO 2005/097230 | 10/2005 |
| WO | WO 2008/057218 | 5/2008 |

\* cited by examiner

*Primary Examiner* — Jason Flick
(74) *Attorney, Agent, or Firm* — Michael W. Ferrell

(57) ABSTRACT

A breast milk collection apparatus includes a milk collection bottle, a breast shield, and a suction transfer assembly for mounting on the bottle. The suction transfer assembly includes a housing for connecting to the vacuum pump and the breast shield. Included in the suction transfer housing is a reversible diaphragm made of a deformable elastomeric material configured with a spiral undulatory configuration. The breast shield includes a unitary funnel member from a relatively rigid polymer as well as an annular deformable lip for enhanced comfort. In one preferred construction, a pump enclosure defines a well for receiving a bottle with deformable gripping projections which adapt to changes in bottle size.

29 Claims, 15 Drawing Sheets

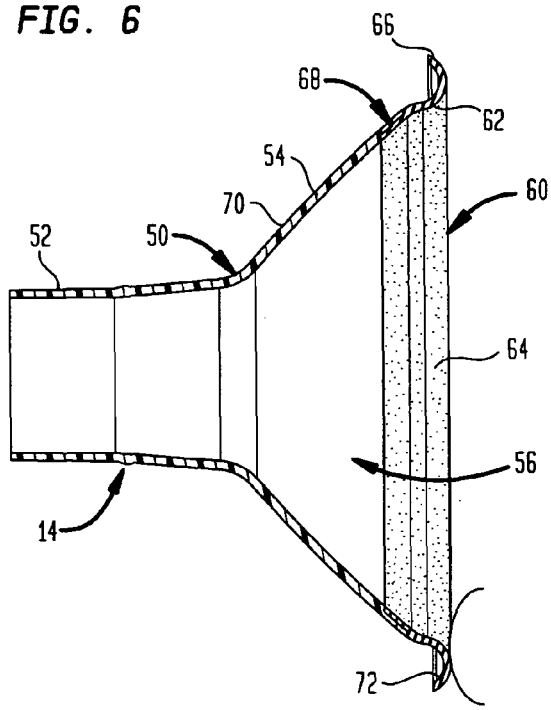
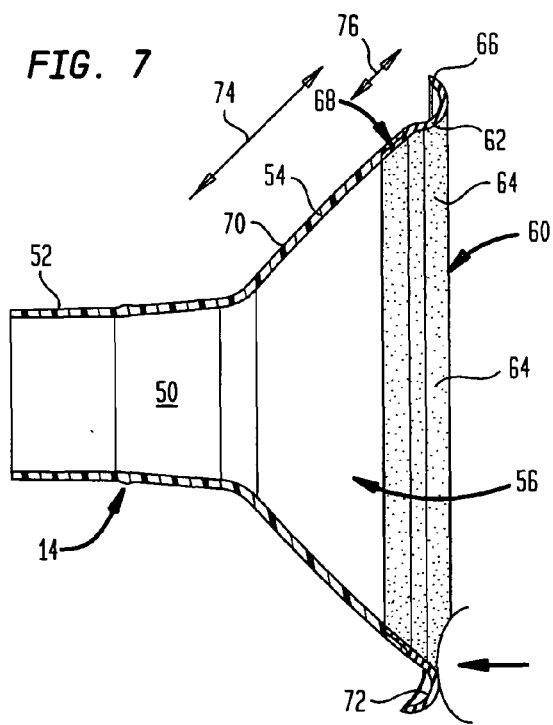

BREAST MILK COLLECTION APPARATUS AND COMPONENTS THEREOF

CLAIM FOR PRIORITY

This non-provisional application claims the benefit of the filing date of U.S. Provisional Patent Application Ser. No. 61/269,283, of the same title, filed Jun. 22, 2009. The priority of U.S. Provisional Patent Application Ser. No. 61/269,283 is hereby claimed and the disclosure thereof is incorporated into this application by reference.

TECHNICAL FIELDS

The present invention relates to a breast milk collection system including a collection bottle with a breast shield having a soft rim and a suction transfer assembly with a reversible barrier diaphragm.

BACKGROUND

Breast milk collection systems are known in the art. There is disclosed in International Publication No. WO 2008/057218 to Luzbetak et al. a vacuum pump with a barrier preventing contamination from entering a vacuum pump air line. The barrier separates part of the pump and is movable between an initial state and the distended state. The barrier is assembled within the pump with a preload which is reported to assist the barrier in returning to its initial state from a distended state. Pump diaphragms with radial features are also known in the art. In this regard, see U.S. Pat. No. 7,363,850 to Becker as well as U.S. Pat. No. 4,809,589 to Bertrand.

Breast pump systems are sometimes provided with different sets of shields to accommodate different breast sizes or shapes. See U.S. Pat. No. 6,723,066 to Larsson et al. entitled "Breastpump With Universal Hood Base and Interchangeable Suction Hoods." In the '066 patent, the suction hoods are funnel shaped shields made of substantially rigid plastic having a tubular part attached to the funnel of different sizes to connect to the same hood base. Rigid breast shields, however, have sometimes been reported to cause discomfort in use. See WO 2005/097230 of Silver as well as U.S. Pat. No. 4,799,922 to Beer et al.

Also known in the art are breast pumps having breast shields made partially of relatively rigid material and partially from a soft material. In this regard, note U.S. Pat. No. 7,413,557 to Samson et al., particularly at Column 6, lines 52 and following, wherein it is reported that a soft material is an integral part of the breast shield or horn, being bonded to the rigid material. The soft material provides one or more regions of elasticity to the horn whereby the user can manipulate the soft region, which in turn stimulates the underlying area of the breast.

While there have been advances in the art, existing systems tend to be relatively cumbersome and difficult to clean and reassemble. Moreover, user comfort is still an issue.

SUMMARY OF INVENTION

There is provided in a first aspect of the invention a breast milk collection system including: (a) a milk collection bottle; (b) a breast shield provided with a unitary funnel member formed from a relatively rigid polymer including a tubular portion and a substantially conical portion for receiving a breast. The conical portion has a substantially conical profile and defines an outer opening. The funnel member also has an annular deformable lip portion formed from an elastomeric material which is secured about the outer opening of the funnel member. The milk collection system also includes (c) a suction transfer assembly for mounting on the collection bottle with: (i) a suction housing member or flange member defining a suction cavity and being adapted for connection to the breast shield; (ii) a vacuum housing member or cap defining a vacuum cavity adapted for assembly with the suction housing member or flange and also adapted for connecting to a vacuum line of a vacuum pump; and (iii) a reversible diaphragm made of a deformable elastomeric material configured to mount between the suction housing member and the vacuum housing member so as to isolate the vacuum cavity from the suction cavity to provide vacuum to the suction cavity from the vacuum cavity upon deformation of the diaphragm under vacuum provided by way of the vacuum pump.

In another aspect of the invention, there is provided a breast shield which includes: (a) a unitary funnel member formed from a relatively rigid polymer including a tubular portion for connecting to the breast milk collection apparatus and a substantially conical portion for receiving a breast having a substantially conical profile and defining an outer opening; and (b) an annular deformable lip portion formed of an elastomeric material secured about the outer opening of the funnel member. The annular deformable lip has an inner proximal portion projecting inwardly with respect to the conical profile of the conical portion of the funnel member and an outer distal portion flaring outwardly with respect to the proximal portion thereof such that the breast shield readily adapts to the breast of a user.

In the preferred embodiment, the reversible diaphragm of the suction transfer assembly has a spiral undulatory structure as described herein.

Further aspects and advantages of the present invention will become apparent from the discussion which follows.

BRIEF DESCRIPTION OF DRAWINGS

The invention is described below in connection with the drawings wherein like numerals designate similar parts. In the drawings:

FIG. 6 is another side view, in section, of the breast shield of FIGS. 4 and 5 schematically illustrating sealing of the breast shield;

FIG. 7 is another side view, in section, of the breast shield of FIGS. 4, 5, and 6, also illustrating sealing action of the breast shield;

DETAILED DESCRIPTION

Figure 1:
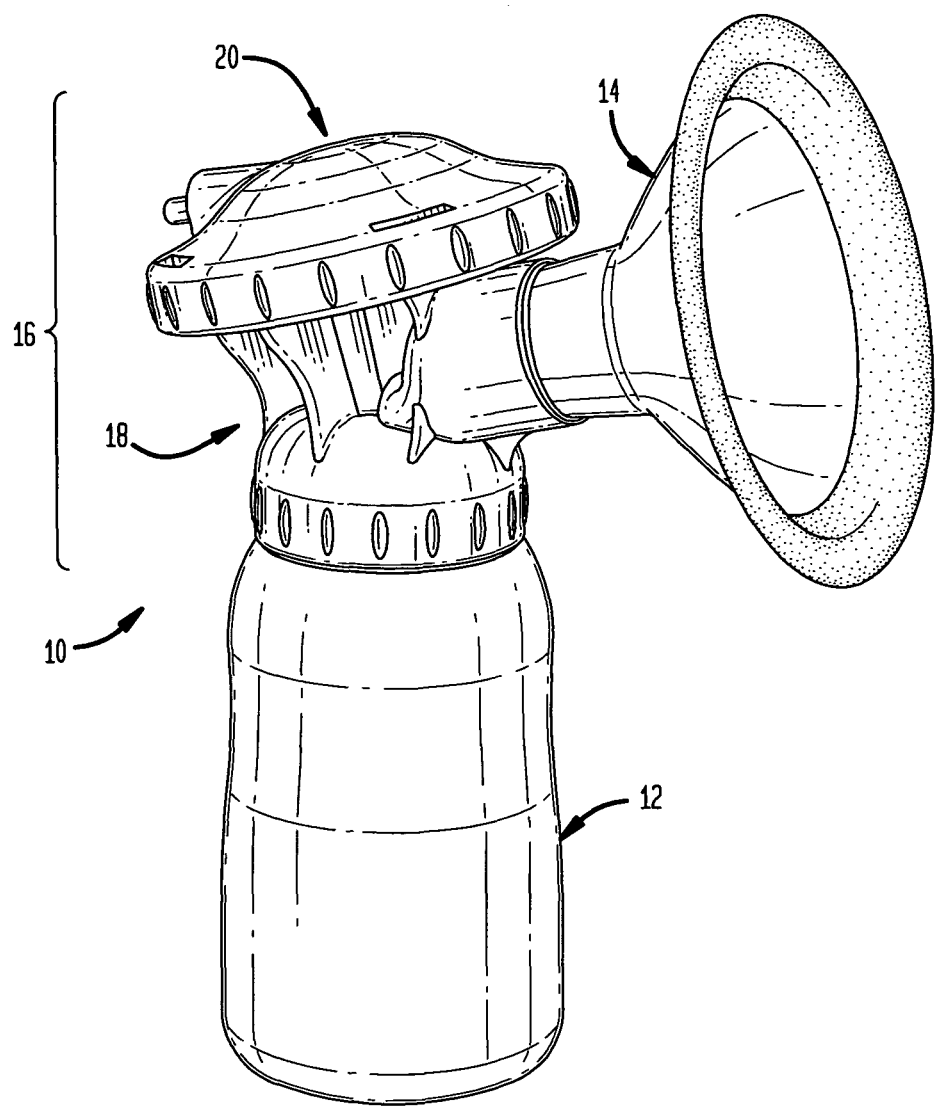
FIG. 1 is a perspective view of a breast milk collection system constructed in accordance with the invention.

The invention is described in detail below for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning.

The terminology "interference-fit seal" refers to a seal between sealing members which are configured such that they are urged into engagement by their geometries. One sealing member thus has a larger dimension or dimensions in the free state than the dimension or dimensions of the cooperating part with which it forms a seal. When the interference-fit seal is formed, the sealing members become the same size and develop a seal through elastic compression, plastic movement of material, or both, much like interference-fit class 5 threads. See *Machinery's Handbook*, R. Green, Ed., $24^{th}$ edition, Industrial Press.

As used herein, the terminology "polyolefin" refers to addition polymers such as polypropylene or polyethylene, but the terms "polypropylene resin" or "polypropylene composition" or like terminology, refers to a composition which is predominately (more than 50 mole %) made up of propylene repeat units and includes melt blends with other resins and additives. Likewise, polyethylene resins are predominately ethylene repeat units while polyethylene terephthalate resins are predominately ethylene terephthalate repeat units. An ethylene/propylene copolymer contains both ethylene and propylene repeat units in the resin and may be made up primarily of repeat units of either species.

Any suitable polypropylene may be used to form various parts. Suitable polypropylenes include: random polymers, isotactic polypropylene, copolymers of propylene and ethylene, for example, wherein the ethylene moiety is less than about 10%, and so forth.

Various polyethylene polymers which may be used, with or without polypropylene, are described at length in the Encyclopedia of Polymer Science & Engineering (2nd Ed.), Vol. 6; pp: 383-522, Wiley, 1986; the disclosure of which is incorporated herein by reference. HDPE refers to high density polyethylene which is substantially linear and has a density of generally greater than 0.94 up to about 0.97 g/cc. LDPE refers to low density polyethylene which is characterized by relatively long chain branching and a density of about 0.912 to about 0.925 g/cc. LLDPE or linear low density polyethylene is characterized by short chain branching and a density of from about 0.92 to about 0.94 g/cc. Finally, intermediate density polyethylene (MDPE) is characterized by relatively low branching and a density of from about 0.925 to about 0.94 g/cc.

Instead of the above noted polypropylene based resinous compositions, polypropylene/polyethylene copolymers with more significant polyethylene content could be used or a polyethylene based composition could be used. Likewise, polyethylene terephthalate based compositions may be used. In still further embodiments, any other suitable polymeric composition is used so long as the composition is sufficiently resilient.

Insofar as the deformable lip of the breast shield and the elastomeric reversible diaphragm are concerned, any suitable elastomers may be used. Due to their durability, silicone rubbers are especially preferred for the diaphragm employed. With respect to the deformable lip of the breast shield, any suitable elastomer may be used. Suitable elastomeric materials include acrylic elastomers; butyl rubber; chlorosulfonated polyethylene; ethylene-propylene rubber; fluorinated elastomers; neoprene; nitrile rubber; polybutadiene; polyethers; polyisoprene; polypentenamers; styrene-butadiene rubber; and thermplastic elastomers. See, also, *Kirk-Othmer Encyclopedia of Chemical Technology*, $3^{rd}$ Ed., Vol. 8 pp. 446-640, the disclosure of which is incorporated herein by reference.

Particularly preferred are those elastomers which may be to "two-shot" injection molded with the more rigid portion of the breast shield, i.e., the funnel member which includes a conical portion and a tubular portion.

Further details will be appreciated from the discussion which follows.

Figure 2:
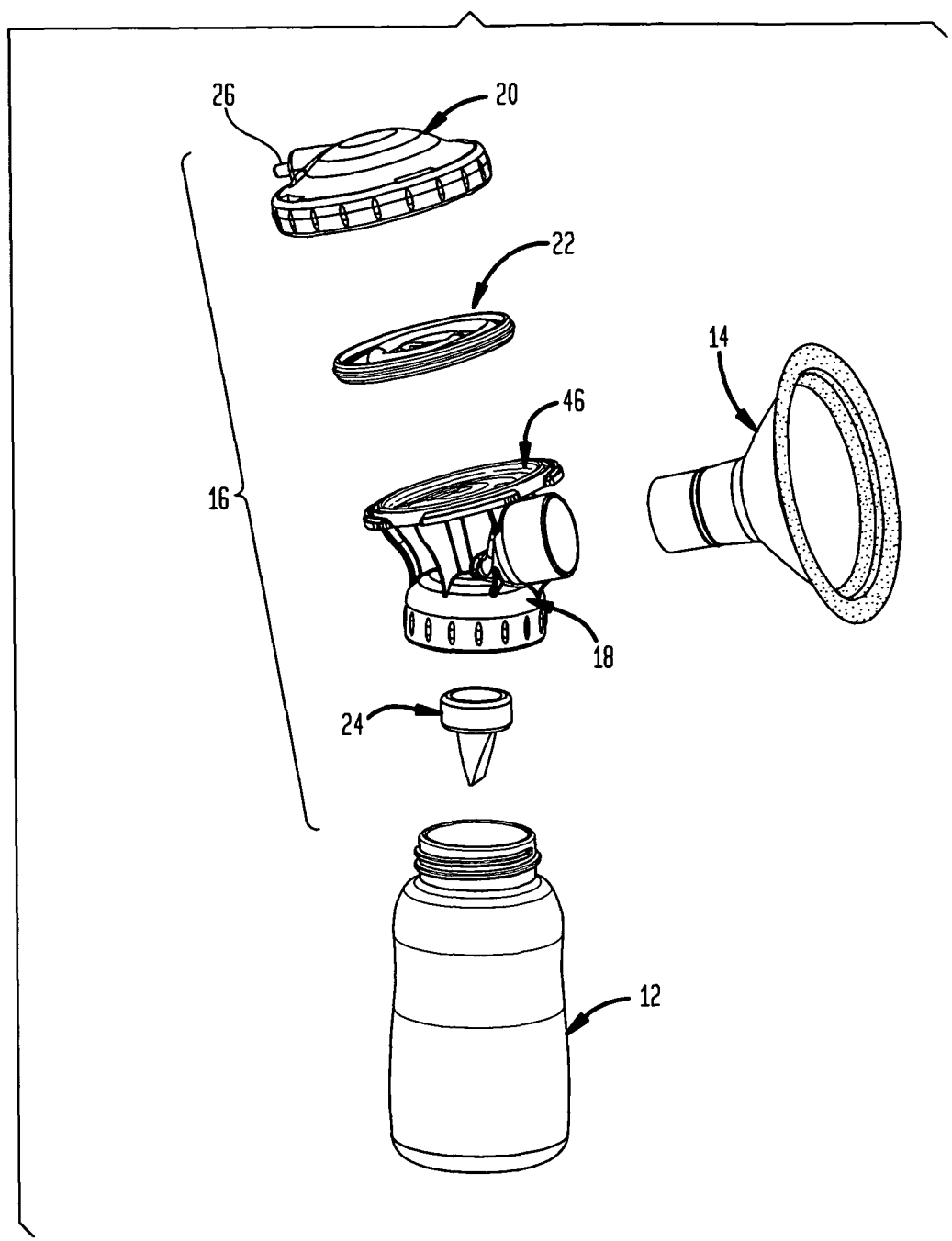
FIG. 2 is an exploded perspective view of the breast milk collection system of FIG. 1.
Figure 3A:
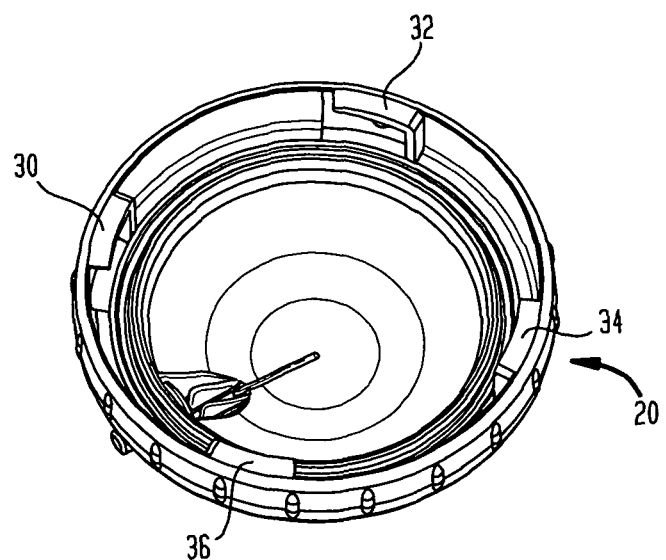
FIGS. 3A-3E are schematic diagrams illustrating assembly options for the breast milk collection system of FIGS. 1 and 2.
Figure 3B:
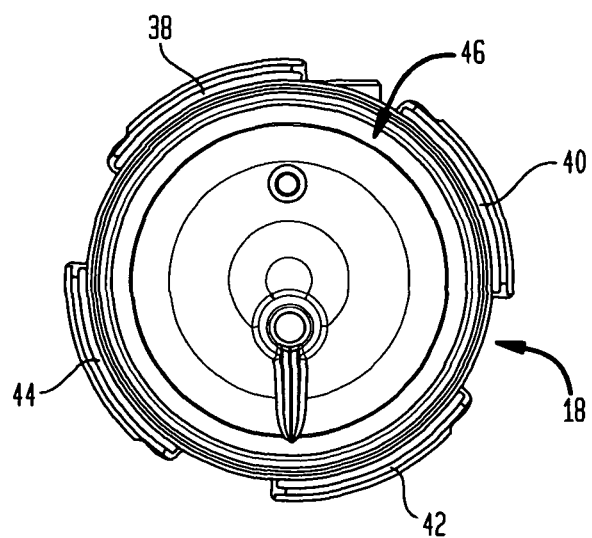
Figure 3C:
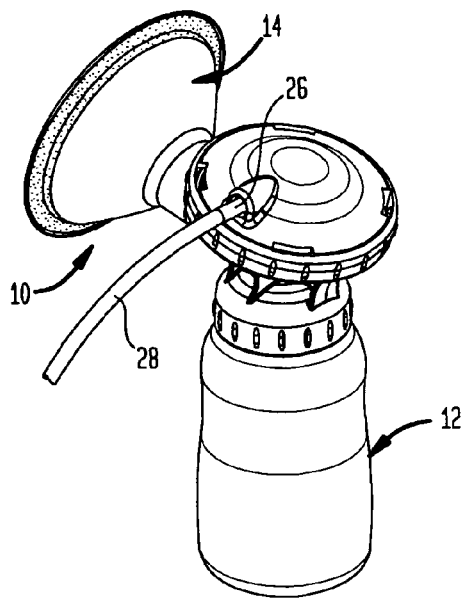
Figure 3D:
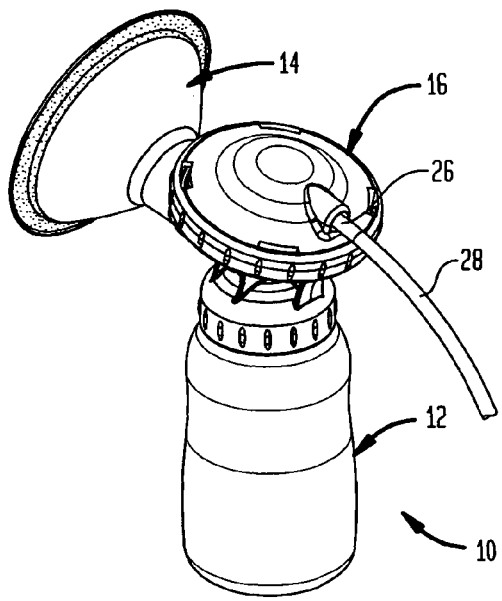
Figure 3E:
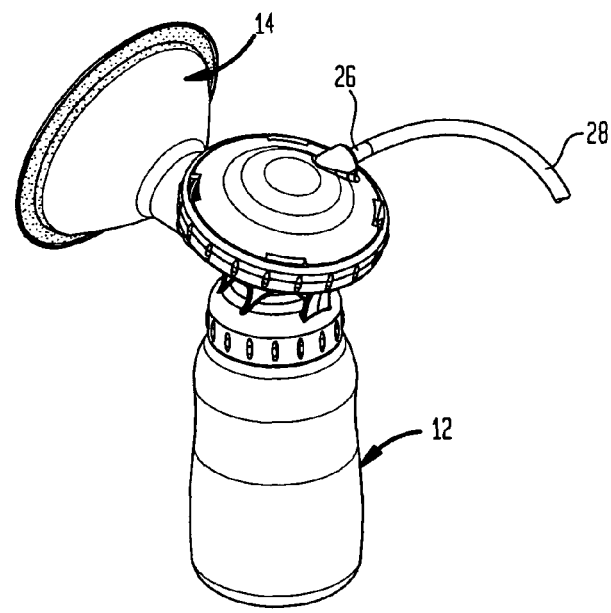
Figure 4:
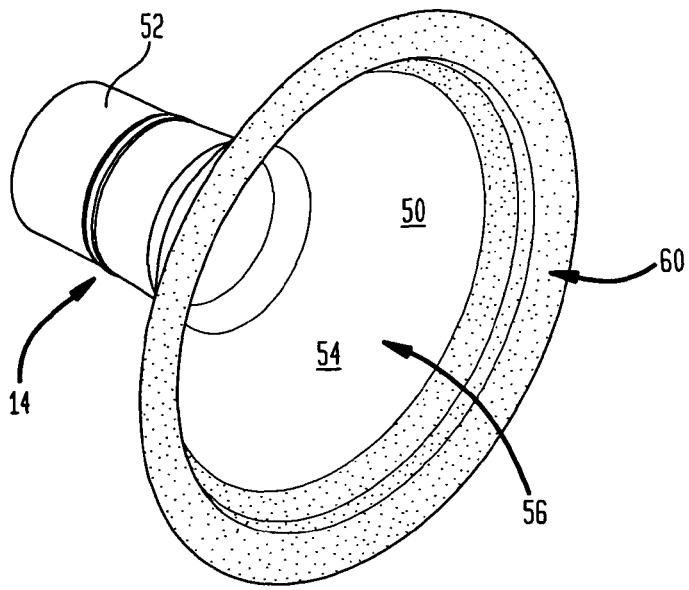
FIG. 4 is a perspective view of a preferred breast shield.

Referring first to FIGS. 1 and 2, there is shown a breast milk collection apparatus 10 which includes a collection bottle 12 as well as a breast shield 14 for placement on a breast. The apparatus includes a suction transfer assembly 16 which has a suction housing member or flange member 18, a vacuum housing member or cap 20, a reversible diaphragm 22, and a one-way valve 24.

The system is constructed such that the suction transfer assembly 16 transfers vacuum through deformable diaphragm 22 as is appreciated by one of skill in the art. To this end, the apparatus is connected to a vacuum pump (not shown) by way of a coupling conduit 26.

Referring additionally to FIGS. 3A-3E, it is seen that the apparatus 10 of the invention provides several options as to connecting to a vacuum pump (not shown) by way of a tube 28, for example. Because it may be desirable to orient conduit 26 in a variety of positions about the top of the apparatus, cap 20 is provided with a plurality of bayonet features 30, 32, 34, and 36 which cooperate with a plurality of ridges 38, 40, 42, and 44 which are located at an upper flange 46 of suction housing member 18. Note that it is apparent from FIGS. 3A-3E that cap 20 may be attached to flange 46 by means of the four bayonet features, i.e., twist to attach, which are equally spaced to allow the user to attach the cap in any one of four possible positions. This allows different options for the pipe position of conduit 26 relative to the other components to provide comfortable options to a user.

It should be appreciated from FIGS. 1-3E that operation of the inventive system may be provided by way of a conventional breast pump which provides a cyclic vacuum pulse to the apparatus via line 28. That is, the vacuum applied by the vacuum pump through line 28 and conduit 26 operates on deformable membrane 22 which distends upwardly into cap 20 from a rest position to provide vacuum to the suction transfer housing 18. To this end, one-way valve 24 closes under vacuum such that the suction is applied to the breast through breast shield 14. Breast shield 14 is sealingly engaged about the breast of the user in order to collect the milk expressed from a lactating breast. The milk is drawn into suction housing 18 when vacuum is applied. When the vacuum is released, valve 24 opens and the collected milk is provided to collection bottle 12. It is seen in the various diagrams that diaphragm 22 acts as a barrier between the vacuum pump connected to line 28 and the suction housing 18, i.e., the collection portions of the apparatus. There is thus provided in accordance with the invention a milk collection apparatus including a milk collection bottle 12, a breast shield 14, and a suction transfer assembly 16.

The various features of these parts are described further in connection with FIGS. 4-10. In FIGS. 4-7 there is shown a breast shield 14 which includes a unitary funnel member 50 which is formed of a relatively rigid polymer such as polypropylene or polyethylene. Funnel member 50 has a tubular portion 52 as well as a generally conical section 54 for receiving a breast. Conical section 54 has a substantially conical profile and defines an outer opening thereof at 56. An annular deformable lip 60 is formed of an elastomeric material, i.e., santoprene or the like and is secured about the outer opening 56 of funnel member 50. The annular deformable lip 60 has an inner proximal portion 62 which projects inwardly a distance 64 with respect to the conical profile of the funnel member 50. The deformable lip also has an outer distal portion 66 that flares outwardly with respect to the proximal portion of the lip. The funnel member is formed of a polyolefin such as polypropylene, and the deformable lip portion is formed of a synthetic elastomer such as santoprene.

Figure 5:
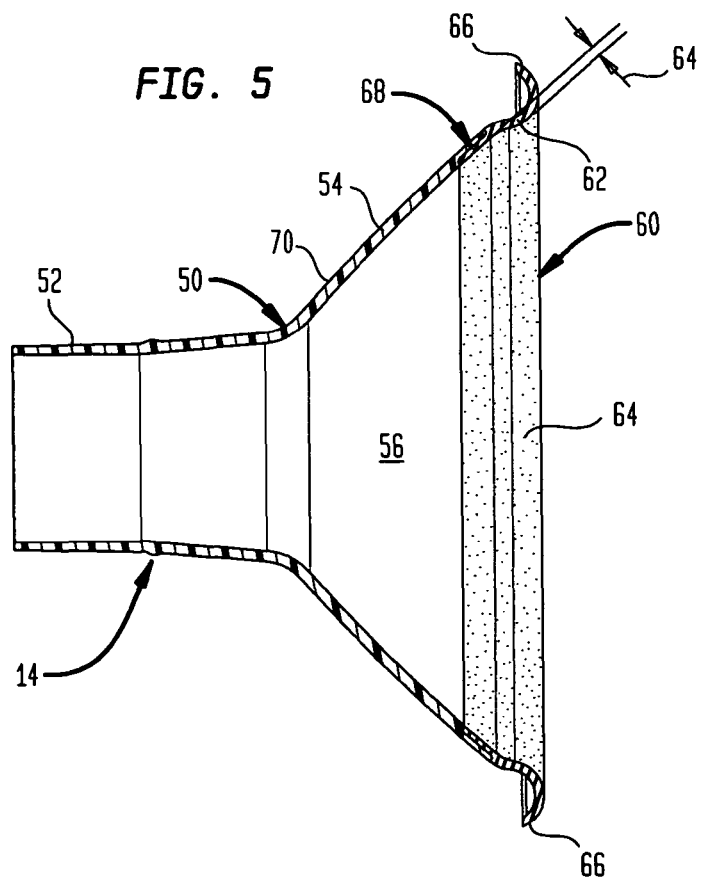
FIG. 5 is a side view, in section, of the breast shield of FIG. 4.

In one preferred embodiment, the breast shield is produced by a two-shot injection molding process whereby the funnel member is injection molded first, and the deformable lip portion is directly adhered to the funnel member of the breast shield by a second shot wherein the elastic material is molded to the relatively rigid funnel member. In one preferred construction, the funnel member and the proximal portion of the annular deformable lip are configured to form a scarfed joint 68 therebetween as is seen in FIGS. 5-7. Scarfed joint 68 may also be referred to as a "lap joint" or "splice joint". Other joint configurations between the materials, such as a simple butt joint may also be used, if so desired. Note that scarfed joint 68 includes overlapping sections of the elastomer and the more rigid polymer, that is to say the thickness of both parts is reduced in the scarfed joint area 68 so as to provide more contact area between the two portions of the breast shield while maintaining a flush inner surface in the interior of the breast shield as shown in FIGS. 4-7 in particular.

Note in the various diagrams that conical section 54 of funnel member 50 is slightly rounded or convex at 70. While the member conical section is substantially conical, this slight rounding provides curvature to conform to the roundness of a breast if so desired. Likewise, the inventive construction having a unitary funnel member is readily adaptable to the manufacture of funnels of different size for attachment to the collection apparatus of the present invention.

A plurality of breast shields may be produced having different sized funnel portions, i.e., different sized conical sections 54 and the same sized tubular portions 52 for connection with the apparatus. In this way, inserts are avoided when it is desired to accommodate breasts of different sizes in the collection apparatus. One may simply substitute another breast shield particularly sized for a particular user.

Among the benefits of the inventive breast shield are improved comfort, more reliable vacuum seal, and the possibility of using color coding if one chose to systematically alter the color of the breast shield in accordance with sizes. Moreover, the breast shield is readily manufactured by a rigid plastic cone in the first shot and a second shot of elastomer on the rim where most consumers complain about conventional breast shields which are overly rigid and cause discomfort. The soft edge of the lip 60 protrudes inwardly a distance 64 as shown in FIG. 5 in particular inwards from the profile of the conical section of the breast shield. That is, it protrudes inwardly toward the breast and helps to improve sealing. The slightly concave shape or curvature conforms the roundness of the breast, again providing comfort over and above that of conventional systems. The soft edge also provides better sealing against uneven parts of the body and different sizes and shapes. This improved sealing is especially achieved by a rolling action of the outer lip when pressed against the body.

This latter feature is shown schematically in FIGS. 6 and 7 at the lower portions of the diagram. To this end, an outer arcuate section 72 protrudes outwardly from the proximal portion of the deformable lip and readily rolls under pressure as shown in FIG. 7 to maintain a seal with very little mechanical pressure applied. Thus, the inventive breast shield is both comfortable and more effective than conventional systems.

The soft edge materials for the deformable lip could include Kraiburg TF4ATL, DryFlex 500450S, or Santoprene 271-55EU. While adhesive may be used in the process, generally the two materials, i.e., the elastomers and the polyolefins, will fuse together with the heat of the two-shot injection molding process.

Generally, the profile of the deformable lip portion has an outward span, i.e., along the conical profile of the shield, of anywhere from about 20% to 40% of an outward span of the conical portion of the funnel member.

In this regard, referring to FIG. 7, it is seen that the outward span of the conical portion of the funnel member extends a distance 74 while the deformable lip 60 extends over an outward conical span 76. Thus, distance 76 is anywhere from about 20% to about 40% of distance 74.

Figure 8:
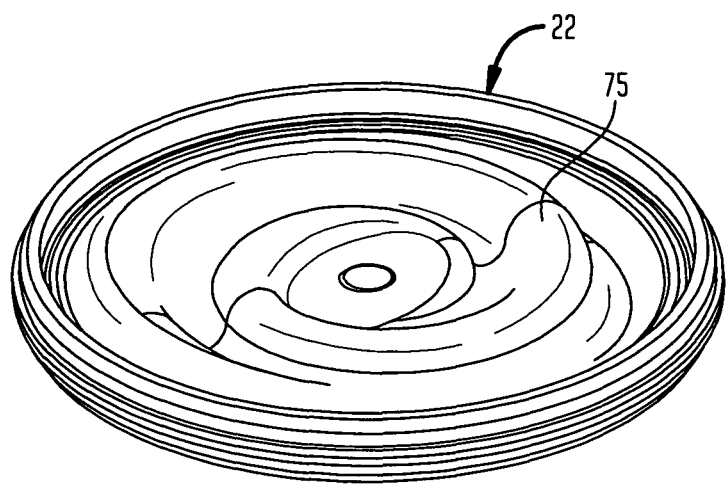
FIG. 8 is a perspective top view of a reversible diaphragm useful in connection with the breast milk collection system of the invention.
Figure 9:
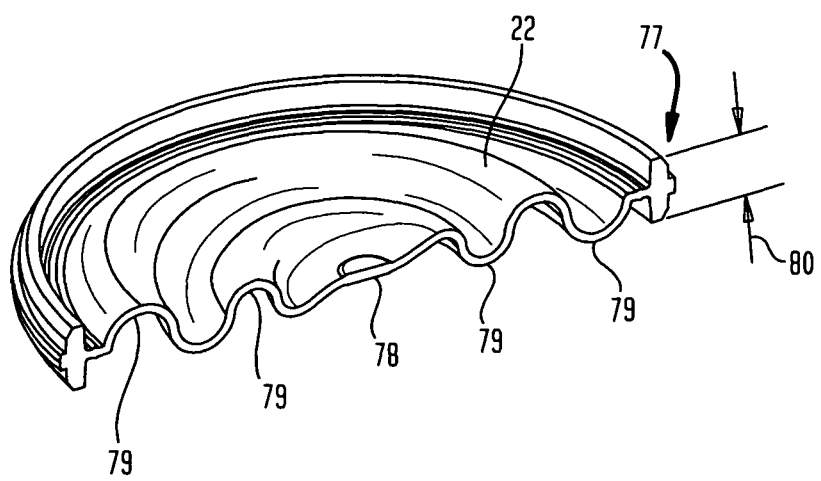
FIG. 9 is a perspective view, partially in section, of the reversible diaphragm of FIG. 8.

Still further features of the inventive system are appreciated by reference to FIGS. 8-11. FIG. 8 shows the diaphragm 22. The diaphragm may be inserted into the apparatus either in an "up" position or in a "down" position. That is in any orientation. When we refer to a reversible diaphragm, we refer to the fact that the diaphragm may be employed in an upwards or a downwards orientation. That is, diaphragm 22 may be inserted with either side up or down. The diaphragm may be made of an elastomer as noted above, or may be made of a silicone rubber material as is known in the art. Suitable silicone rubber materials are described in *Kirk-Othmer Encyclopedia of Chemical Technology*, $3^{rd}$ Ed, Vol. 20, pp. 943-53, the disclosure of which is incorporated herein by reference.

The seal formed between the parts is generally a compression/interference seal as described hereinafter and thus does not depend upon a tight fit between the suction housing member and the vacuum housing member or cap. It is preferred that the diaphragm is retained on the flange of the suction housing when the cap is removed as is also described hereinafter.

As is appreciated by one of skill in the art, as the diaphragm moves, vacuum is transferred from the external vacuum pump to the breast such that the diaphragm acts as a barrier to stop any milk from being sucked back into the pump.

FIG. 8 is a top perspective view of reversible diaphragm 22. Reversible diaphragm 22 has spiral undulations as is seen particularly in FIGS. 8 and 9. The spiral undulation may be formed from a single spiral pattern 75 which extends generally from the center of the diaphragm spirally outwardly to the outer edges thereof. The structure is perhaps best seen in FIG. 9 where the undulation is seen in perspective and section over a diameter through the center of the diaphragm, defining a plurality of arched ridges 79.

Figure 10:
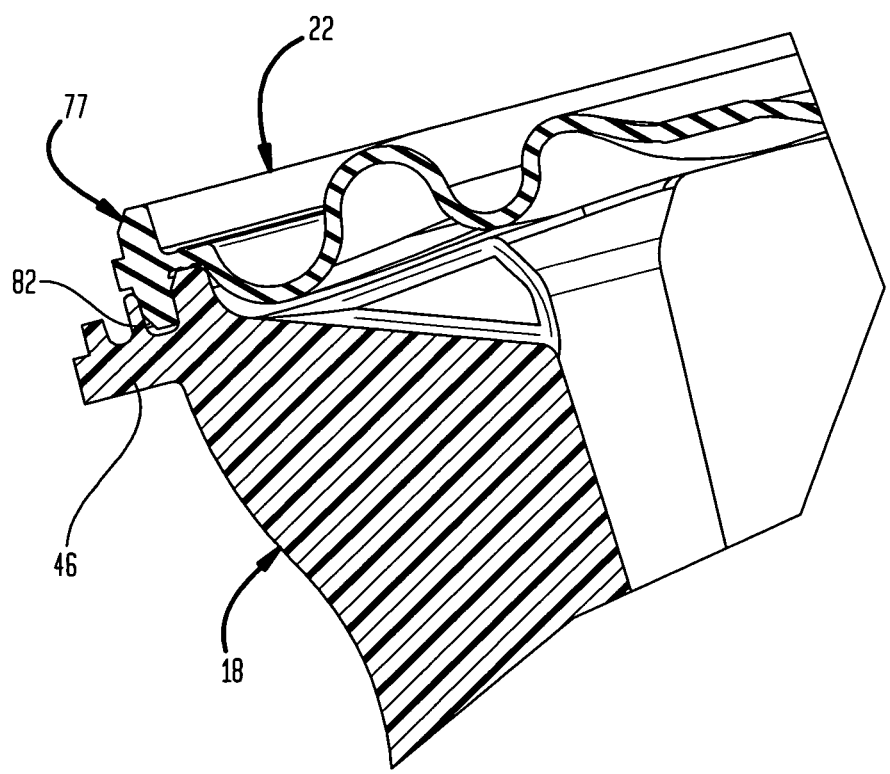
FIGS. 10 and 11 are schematic diagrams illustrating the interference fit seal of the diaphragm of FIGS. 8 and 9 with the suction housing member and vacuum housing member.
Figure 11:
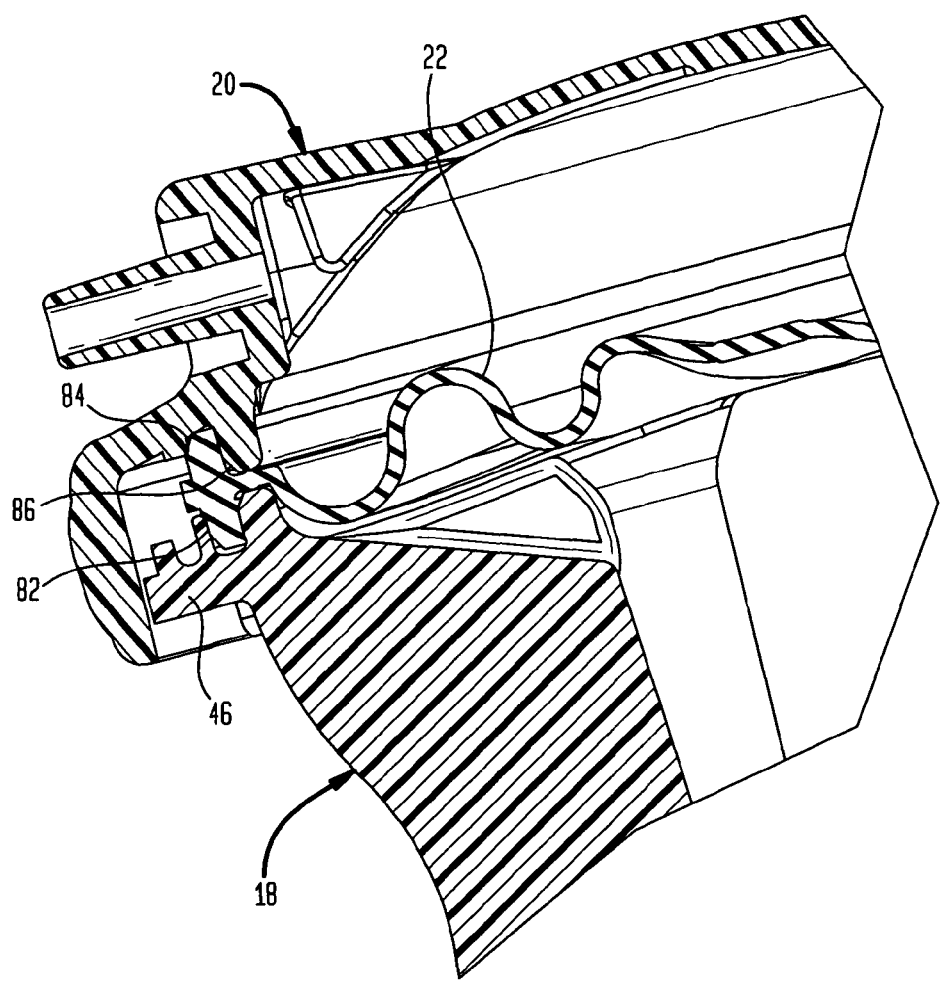

The undulations allow the diaphragm to expand and contract effectively to transfer vacuum from the pump to the suction chamber. Indeed, the performance and its effectiveness of the diaphragm have been surprisingly superior. Note, also, in FIG. 9 that the diaphragm has a thick edge to give it strength for handling and allow it to keep its shape during insertion into the suction transfer assembly of the inventive apparatus 10. To this end the reversible diaphragm 22 has a fortified rim 77 which is at least two times thicker than the central portions of the diaphragm indicated at 78 on FIG. 9. In most cases the fortified rim will have a thickness 80 which is anywhere from 2-5 times the thickness of the diaphragm at 78. The fortified rim 77 also provides a means for forming interference/fit seals with the housing members of the system. In order to assemble the suction assembly, a user places the diaphragm on flange 46, pressing it gently into position as is shown in FIG. 10. The diaphragm rim is slightly thicker than a mounting groove 82 in flange 46 such that an interference-fit seal is provided. After the diaphragm is placed on flange 46, the cap 20 or vacuum housing member is applied over the diaphragm, and the bayonet features are used to lock the assembly into place as was discussed above in connection with FIGS. 3A-3E. Cap 20 also has a mounting groove 84 which forms an interference/fit seal with the diaphragm as well. This particular feature is seen in FIG. 11 at 86. In general, the fit with the cap is based on the same interference/fit principle as the engagement of the diaphragm with the flange of the suction housing member or flange member, but the engagement has more angles and there is less interference. Thus, when the cap is removed, the diaphragm preferably tends to remain on the flange for ease of handling.

Figure 12:
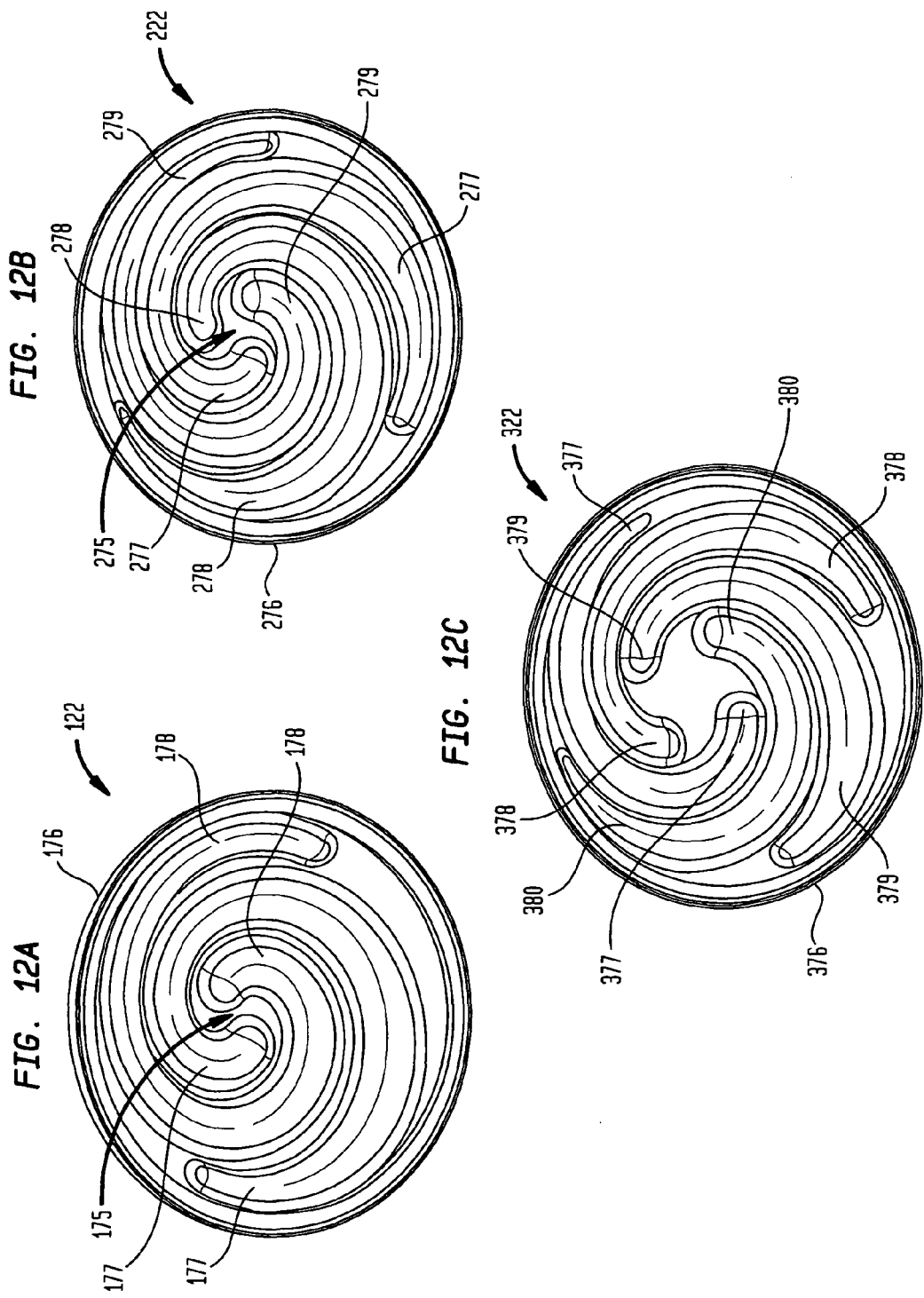
FIGS. 12A-12C are alternate constructions of a barrier diaphragm of the breast milk collection apparatus.
Figure 13:
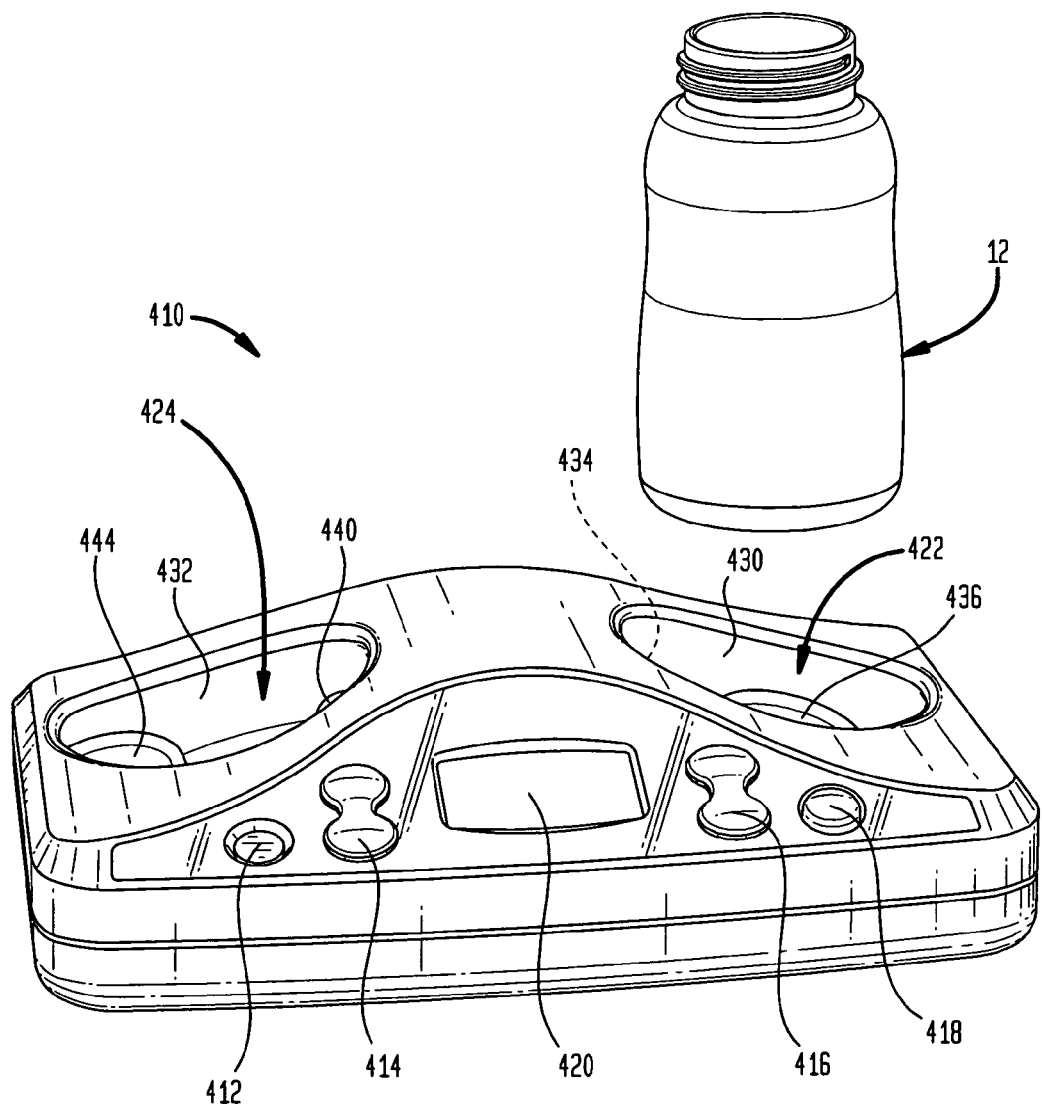
FIG. 13 is a perspective view of a pump base with a well for receiving a collection bottle.
Figure 14:
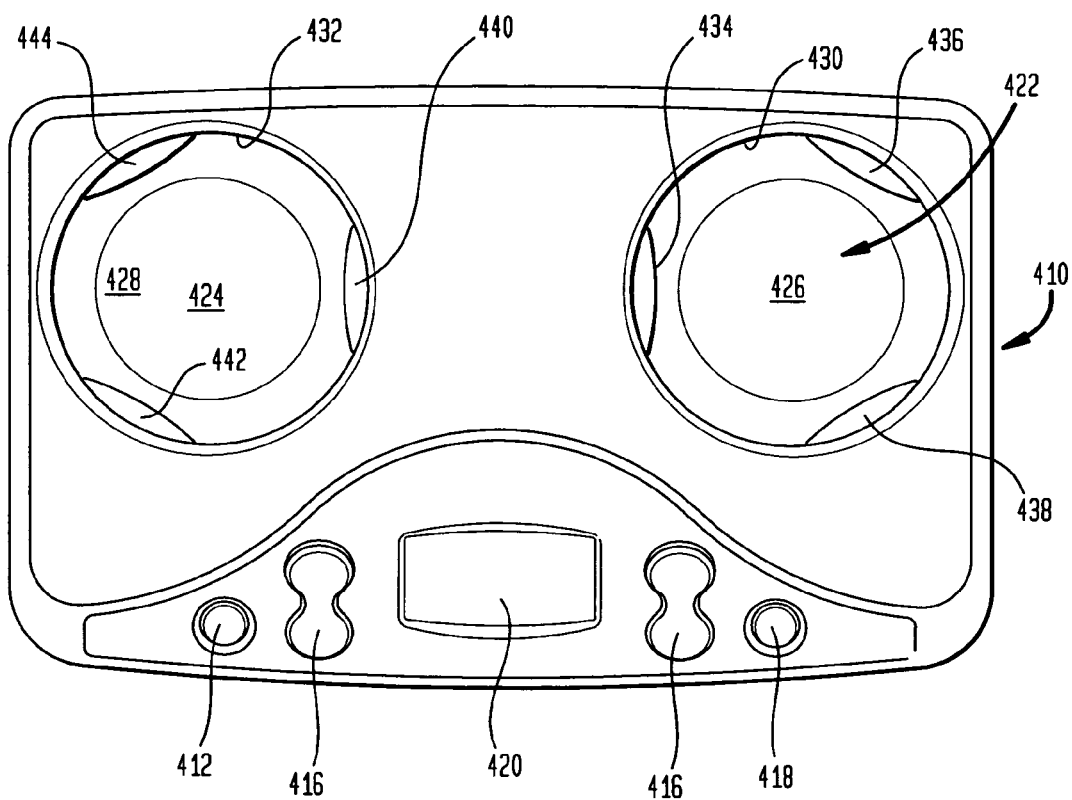
FIG. 14 is a plan view of the pump base of FIG. 13.

Instead of a "single-start" spiral as shown in FIGS. 8-11, it is also possible to use "multi-start" spirals as shown in FIGS. 12A, 12B and 12C. FIG. 12A shows a diaphragm 122 which may be used in place of diaphragm 22 which has a two-start spiral configuration 175 which has 2 distinct spirals 177, 178 which begin at the center of the diaphragm and continue outwardly to fortified rim 176. Similarly, FIG. 12B shows a diaphragm 222 which may be used in place of diaphragm 22 which includes a three-start spiral configuration 275 which has 3 distinct spirals 277, 278, 279 which begin at center and extend spirally outwardly to fortified rim 276. In a still further embodiment, FIG. 12C shows a diaphragm 322 which may be used in place of diaphragm 22 which includes a four-start spiral configuration 375 which has 4 distinct spirals 377, 378, 379 and 380 which begin at center and extend outwardly to fortified rim 376.

In still yet another aspect of the invention, illustrated in FIGS. 13-17, there is provided a pump housing or enclosure 410 provided with control switches 412, 414, 416 and 418, as well as a display 420. Housing 410 includes 2 wells 422, 424 with bottom portions 426, 428 for supporting bottle 12. Wells 422, 424 have generally cylindrical sidewalls 430, 432, each of which have 3 deformable sidewall projections or lugs 434, 436, 438, 440, 442, 444 of generally ovoid shape; that is, ovoid sectional shape. These projections provide variable engagement surfaces for securing a bottle such as bottle 12. The engagement surfaces automatically adapt to relatively small changes in bottle diameter as the bottle shrinks after repeated washing in hot water, for example, up to a 5%, 7% or 10% diameter reduction; that is, the engagement surfaces can accommodate and firmly engage the bottle, urging it downwardly toward the bottom of the well so as to prevent/reduce tipping and spills, even when the bottle shrinks substantially. A bottle diameter shrink anywhere from 1% to 10% in diameter, for example, will not prevent a firm seat in the wells because of the deformable projections. In other words, the bottle will remain firmly gripped by the projections despite substantial shrinkage. We refer to this property as "bottle shrink tolerance".

Figure 15:
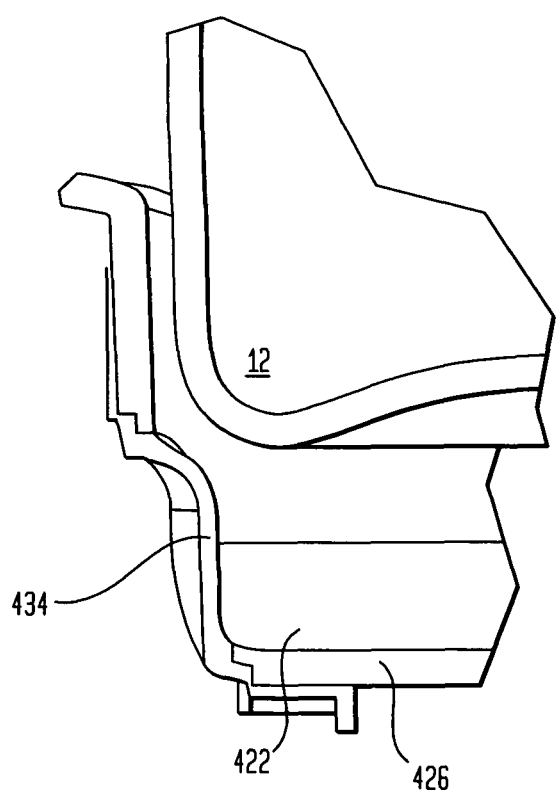
FIGS. 15-17 are schematic details illustrating a deformable sidewall projection of a well of the pump base gripping different size bottles.
Figure 16:
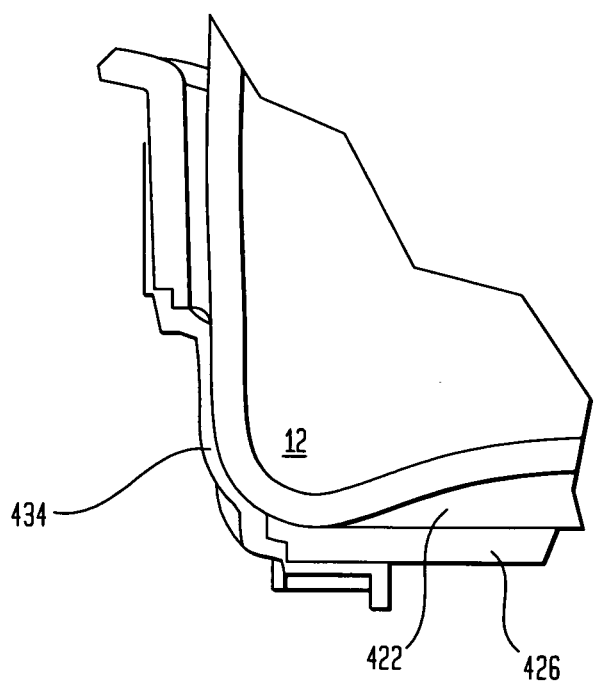
Figure 17:
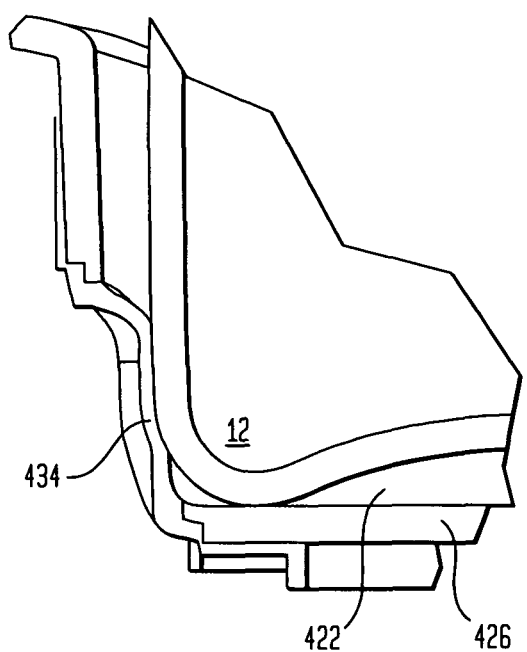

This aspect is shown in FIGS. 15-17 which are schematic diagrams illustrating bottle 12 being advanced into well 422 and being engaged by deformable ovoid projections such as projection 434.

In FIG. 15, a nominal diameter bottle (i.e. prior to shrinking) is shown poised above the well and deformable ovoid projection 434 of well 422.

In FIG. 16, it is seen that the bottle firmly engages and deforms the ovoid projection, thus being snuggly engaged in the well and bulging the ovoid projection outwardly.

In FIG. 17, bottle 12 has been shrunken about 7% in bottle diameter. It is also shown engaged in the well. Here, deformable projection 434 still firmly engages the bottle; however, the projection is deformed much less, that is bulges outwardly much less.

Thus, there is provided in a breast milk collection apparatus an enclosure adapted to receive a bottle, wherein the enclosure includes a well having a sidewall and a bottom for receiving a bottle, the sidewall provided with a plurality of bulbous deformable projections, the spacing and arrangement of said bulbous deformable projections is adapted to grip bottles over a range of sizes with at least a 3% bottle size tolerance to accommodate shrinkage of said bottles and to urge bottles within said bottle size tolerance against said bottom of said well in a preferred embodiment.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A breast milk collection apparatus comprising:
   (a) a milk collection bottle;
   (b) a breast shield including:
      (i) a unitary funnel member formed from a relatively rigid polymer including a tubular portion and a substantially conical portion for receiving a breast, the conical portion having a substantially conical profile and defining an outer opening; and
      (ii) an annular deformable lip portion consisting of elastomeric material secured about the outer opening of the funnel member, the deformable lip portion extending outwardly a substantial distance with respect to the conical profile of the funnel member of relatively rigid polymer;
      wherein the annular deformable lip portion and the unitary funnel member are joined by way of a scarfed joint which includes overlapping sections of the elastomeric material and the relatively rigid polymer, such that a thickness of each of the elastomeric material and the relatively rigid polymer is reduced in the scarfed joint so as to provide more contact area between the annular deformable lip portion and the unitary funnel member of the breast shield, while maintaining a flush inner surface in an interior of the breast shield across the scarfed joint; and
   (c) a suction transfer assembly for mounting on the collection bottle including:
      (i) a suction housing member defining a suction cavity and being adapted for connection to the breast shield;
      (ii) a vacuum housing member defining a vacuum cavity adapted for assembly with the suction housing member and also adapted for connecting to a vacuum line of a vacuum pump; and
      (iii) a diaphragm made of a deformable elastomeric material configured to mount between the suction housing member and the vacuum housing member so as to isolate the vacuum cavity from the suction cavity and to provide vacuum to the suction cavity from the vacuum cavity upon deformation of the diaphragm.

2. The breast milk collection apparatus according to claim 1, wherein the breast shield further comprises:
(a) the unitary funnel member formed from a polypropylene polymer including a the tubular portion for connecting to the suction transfer assembly and the substantially conical portion; and
(b) the annular deformable lip portion formed of a synthetic elastomer material secured about the outer opening of the funnel member, the annular deformable lip having an inner proximal portion projecting inwardly with respect to the conical profile of the conical portion of the funnel member and an outer distal portion flaring outwardly with respect to the proximal portion thereof.

3. The breast milk collection apparatus according to claim 1, wherein the breast shield further comprises:
(a) the unitary funnel member formed from the relatively rigid polymer including the tubular portion for connecting to the suction transfer assembly and the substantially conical portion; and
(b) the annular deformable lip portion formed of the elastomeric material secured about the outer opening of the funnel member, the annular deformable lip having an inner proximal portion projecting inwardly with respect to the conical profile of the conical portion of the funnel member and an outer distal portion flaring outwardly with respect to the proximal portion thereof.

4. The breast milk collection apparatus according to claim 3, wherein the funnel member is formed of polyolefin and the deformable lip portion is formed of synthetic elastomer.

5. The breast milk collection apparatus according to claim 3, wherein the funnel member is formed of polypropylene.

6. The breast milk collection apparatus according to claim 3, wherein the funnel member is produced by a two-shot injecting molding process whereby the deformable lip portion is directly adhered to the funnel member of the breast shield.

7. The breast milk collection apparatus according to claim 3, wherein the substantially conical portion of the funnel member has a rounded profile.

8. The breast milk collection apparatus according to claim 3, wherein the outer distal portion of the deformable lip has an arched profile.

9. The breast milk collection apparatus according to claim 3, wherein a profile of the deformable lip portion of the funnel member has an outward span of from 20% to 40% of an outward span of the conical portion of the funnel member.

10. The breast milk collection apparatus according to claim 1, wherein the diaphragm of the suction transfer assembly is reversible and has a spiral undulatory structure.

11. The breast milk collection apparatus according to claim 10, wherein the reversible diaphragm is made of a silicone rubber material.

12. The breast milk collection apparatus according to claim 10, wherein the reversible diaphragm has a fortified rim more than 2 times thicker than central portions of the diaphragm.

13. The breast milk collection apparatus according to claim 12, wherein the suction housing member has a mounting groove adapted to form an interference-fit seal with the reversible diaphragm.

14. The breast milk collection apparatus according to claim 12, wherein the vacuum housing member has a mounting groove adapted to form an interference-fit seal with the reversible diaphragm.

15. The breast milk collection apparatus according to claim 12, wherein the suction housing member and the vacuum housing member both have mounting grooves adapted to form interference-fit seals with the reversible diaphragm.

16. The breast milk collection apparatus according to claim 15, wherein the reversible diaphragm, the suction housing member and the vacuum housing member are configured to form a compression seal upon assembly of the suction housing member and the vacuum housing member.

17. The breast milk collection apparatus according to claim 15, wherein the mounting groove of the suction housing member provides more interference with the reversible diaphragm then the mounting groove of the vacuum housing member.

18. The breast milk collection apparatus according to claim 10, wherein the vacuum housing member or the suction housing member has a plurality of bayonet mounting features which are configured to provide alternative relative assembly positions of the vacuum housing member and the suction housing member.

19. The breast milk collection apparatus according to claim 1, further comprising an enclosure, wherein the enclosure includes a well for receiving the bottle with a bottom and a sidewall provided with a plurality of deformable projections adapted to grip the bottle with at least a 3% bottle diameter tolerance to accommodate shrinkage of the bottle.

20. The breast milk collection apparatus according to claim 19, wherein the deformable projections are adapted to grip the bottle with at least a 5% bottle diameter tolerance to accommodate shrinkage of the bottle.

21. The breast milk collection apparatus according to claim 19, wherein the deformable projections are adapted to grip the bottle with at least a 7% bottle diameter tolerance to accommodate shrinkage of the bottle.

22. The breast milk collection apparatus according to claim 19, wherein the sidewall of the well has 3 deformable projections.

23. The breast milk collection apparatus according to claim 22, wherein the deformable projections are ovoid shaped.

24. The breast milk collection apparatus according to claim 19, wherein the deformable projections are bulbous projections.

25. The breast milk collection apparatus according to claim 19, wherein the deformable projections are operative to urge the bottle downwardly toward the bottom of the well when it is seated in the well.

26. The breast milk collection apparatus according to claim 1, further comprising an enclosure adapted to receive a bottle, wherein the enclosure includes a well having a sidewall and a bottom for receiving a bottle, said well having a sidewall provided with a plurality of bulbous deformable projections, the spacing and arrangement of said bulbous deformable projections being adapted to grip bottles over a range of sizes with at least a 3% bottle size tolerance to accommodate shrinkage of said bottles and to urge bottles within said bottle size tolerance against said bottom of said well.

27. The breast milk collection apparatus according to claim 26, wherein the spacing and arrangement of the bulbous deformable projections are adapted to grip bottles over a range of sizes with at least a 5% bottle size tolerance to accommodate shrinkage of said bottles and to urge bottles within said bottle size tolerance against said bottom of said well.

28. The breast milk collection apparatus according to claim 26, wherein the spacing and arrangement of the bulbous deformable projections are adapted to grip bottles over a range of sizes with at least a 7% bottle size tolerance to accommodate shrinkage of said bottles and to urge bottles within said bottle size tolerance against said bottom of said well.

29. The breast milk collection apparatus according to claim 1, wherein a profile of the deformable lip portion of the funnel member has an outward span of from 20% to 40% of an outward span of the conical portion of the funnel member.

* * * * *